United States Patent
Petereit et al.

(10) Patent No.: US 6,878,387 B1
(45) Date of Patent: Apr. 12, 2005

(54) COATED MEDICAMENT FORMS WITH CONTROLLED ACTIVE SUBSTANCE RELEASE

(75) Inventors: Hans-Ulrich Petereit, Darmstadt (DE); Thomas Beckert, Darmstadt (DE); Eva Lynenskjold, Copenhagen (DK)

(73) Assignee: Roehm GmbH & Co KG, Darmstadt (DE)

( * ) Notice: Subject to any disclaimer, the term of this patent is extended or adjusted under 35 U.S.C. 154(b) by 0 days.

(21) Appl. No.: 09/787,438

(22) PCT Filed: Sep. 28, 1999

(86) PCT No.: PCT/EP99/07179

§ 371 (c)(1),
(2), (4) Date: Apr. 12, 2001

(87) PCT Pub. No.: WO00/19984

PCT Pub. Date: Apr. 13, 2000

(30) Foreign Application Priority Data

Oct. 2, 1998 (DE) .......................... 198 45 358

(51) Int. Cl.⁷ .............................. A61K 9/14; A61K 9/16; A61K 9/48; A61K 9/64; A61K 9/46
(52) U.S. Cl. ....................... 424/490; 424/451; 424/456; 424/458; 424/459; 424/464; 424/465; 424/469; 424/471; 424/489
(58) Field of Search ................................. 424/489, 490, 424/464, 451, 456, 458, 459, 465, 469, 471

(56) References Cited

U.S. PATENT DOCUMENTS

| | | | | |
|---|---|---|---|---|
| 5,051,262 A | * | 9/1991 | Panoz et al. ................. | 424/468 |
| 5,137,733 A | * | 8/1992 | Noda et al. ................... | 424/497 |
| 5,292,522 A | * | 3/1994 | Petereit et al. .............. | 424/490 |
| 5,395,628 A | | 3/1995 | Noda et al. | |
| 5,681,584 A | * | 10/1997 | Savastano et al. .......... | 424/473 |
| 5,948,440 A | * | 9/1999 | Arora et al. ................. | 424/468 |
| 6,159,504 A | * | 12/2000 | Kumabe ..................... | 424/489 |

FOREIGN PATENT DOCUMENTS

| | | |
|---|---|---|
| EP | 0 068 191 | 1/1983 |
| EP | 0 148 811 | 7/1985 |
| EP | 0 225 085 | 6/1987 |
| EP | 0 436 370 | 7/1991 |
| EP | 0 640 341 | 3/1995 |
| EP | 0 640 341 A1 * | 3/1995 |

* cited by examiner

*Primary Examiner*—Thurman K. Page
*Assistant Examiner*—S. Tran
(74) *Attorney, Agent, or Firm*—Oblon, Spivak, McClelland, Maier & Neustadt, P.C.

(57) ABSTRACT

The invention relates to a pharmaceutical preparation consisting of: (a) a core containing an active substance, optionally an excipient and common pharmaceutical additives in addition to the salt of an inorganic acid whose proportion in the weight of the core ranges from 2.5 to 97% by weight and (b) and outer film coating consisting of one or more (meth)acrylate copolymers and optionally common pharmaceutical adjuvants, wherein 40 to 100% by weight of the (meth)acrylate copolymers consist of 93 to 98% by weight of radically polymerized C1- to C4-alkylesters of acrylic or methacrylic acid and 7 to 2% by weight of (meth)acrylate monomers with a quaternary ammonium group in the alkyl radical and that may be optionally present in a mixture consisting of 1 to 60% by weight of one or more additional (meth)acrylate copolymers different from the above-mentioned (meth)acrylate copolymers, consisting of 85 to 100% by weight of a radically polymerized C1- to C4-alkylesters of acrylic orethacrylic acid and optionally and optionally up to 15% by weight of additional (meth)acrylate monomers with basic groups or acid groups in the alkyl radical.

19 Claims, 5 Drawing Sheets

COATED MEDICAMENT FORMS WITH CONTROLLED ACTIVE SUBSTANCE RELEASE

The invention relates to the art of coated pharmaceutical forms with controlled active principle release.

PRIOR ART

European Patent Application 0463877 describes pharmaceutical compositions with delayed active principle release, comprising a core with a pharmaceutical active principle and a single-layer coating film of a hydrophobic salt and a water-insoluble copolymer of ethyl acrylate, methyl methacrylate and trimethylammoniumethyl methacrylate chloride. The hydrophobic salt can be, for example, Ca or Mg stearate. Sigmoidal release curves are obtained. European Patent Applications 0225085, 0122077 and 0123470 describe the use of organic salts in pharmaceutical cores provided with various coatings from organic solutions. Substantially sigmoidal release characteristics are found. European Patent Application 0436370 describes pharmaceutical compositions with delayed active principle release comprising a core with a pharmaceutical active principle and an organic acid and an outer coating film which was applied by aqueous spraying and is a copolymer of ethyl acrylate, methyl methacrylate and trimethylammoniumethyl methacrylate chloride. Sigmoidal release curves are obtained in this case also. The use of organic acids in the salt form is not considered in any of the cited documents.

OBJECT AND ACHIEVEMENT

Figure 1:
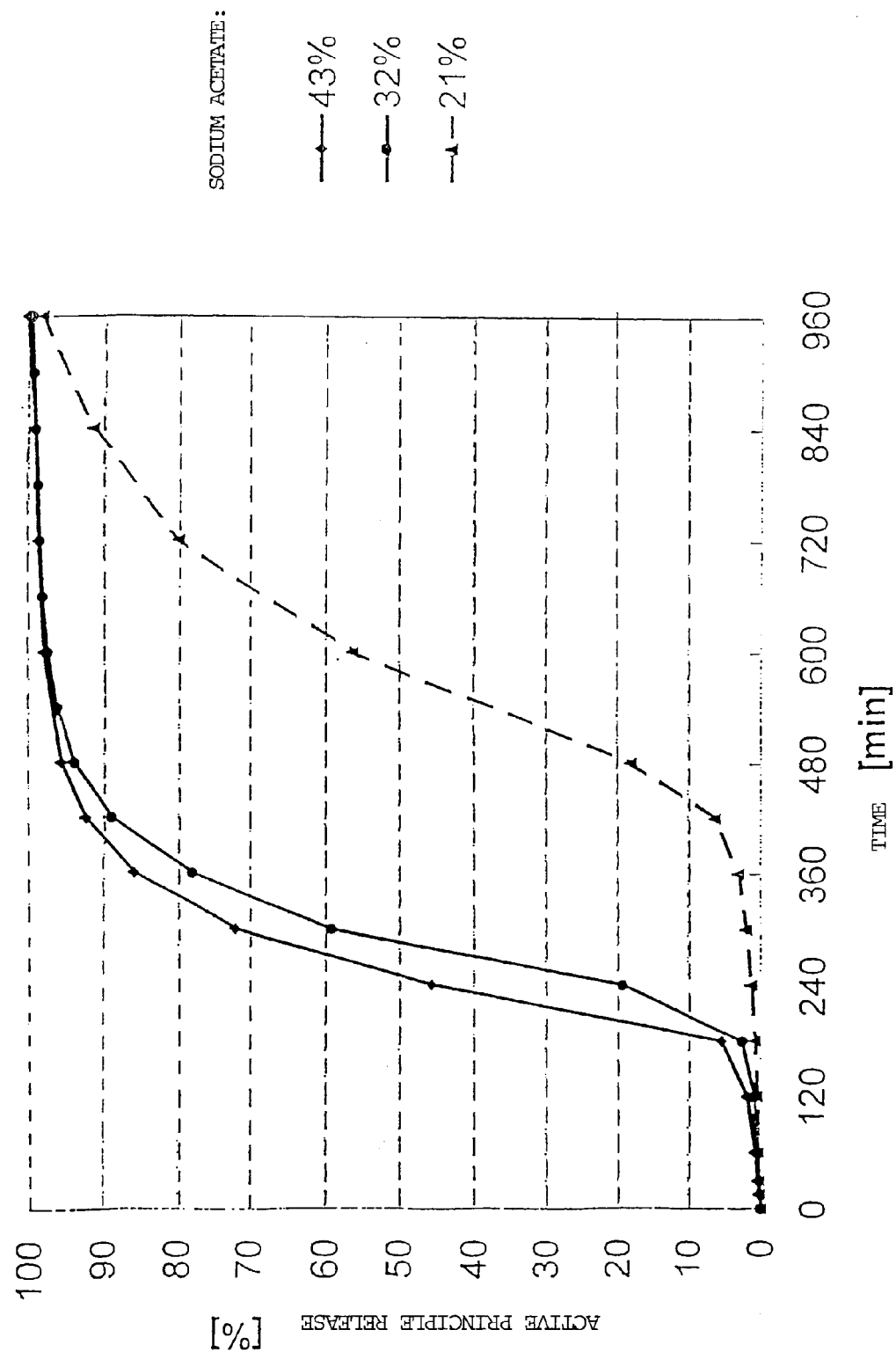
FIGS. 1–5 are release curves for examples 1–5, respectively.
Figure 2:
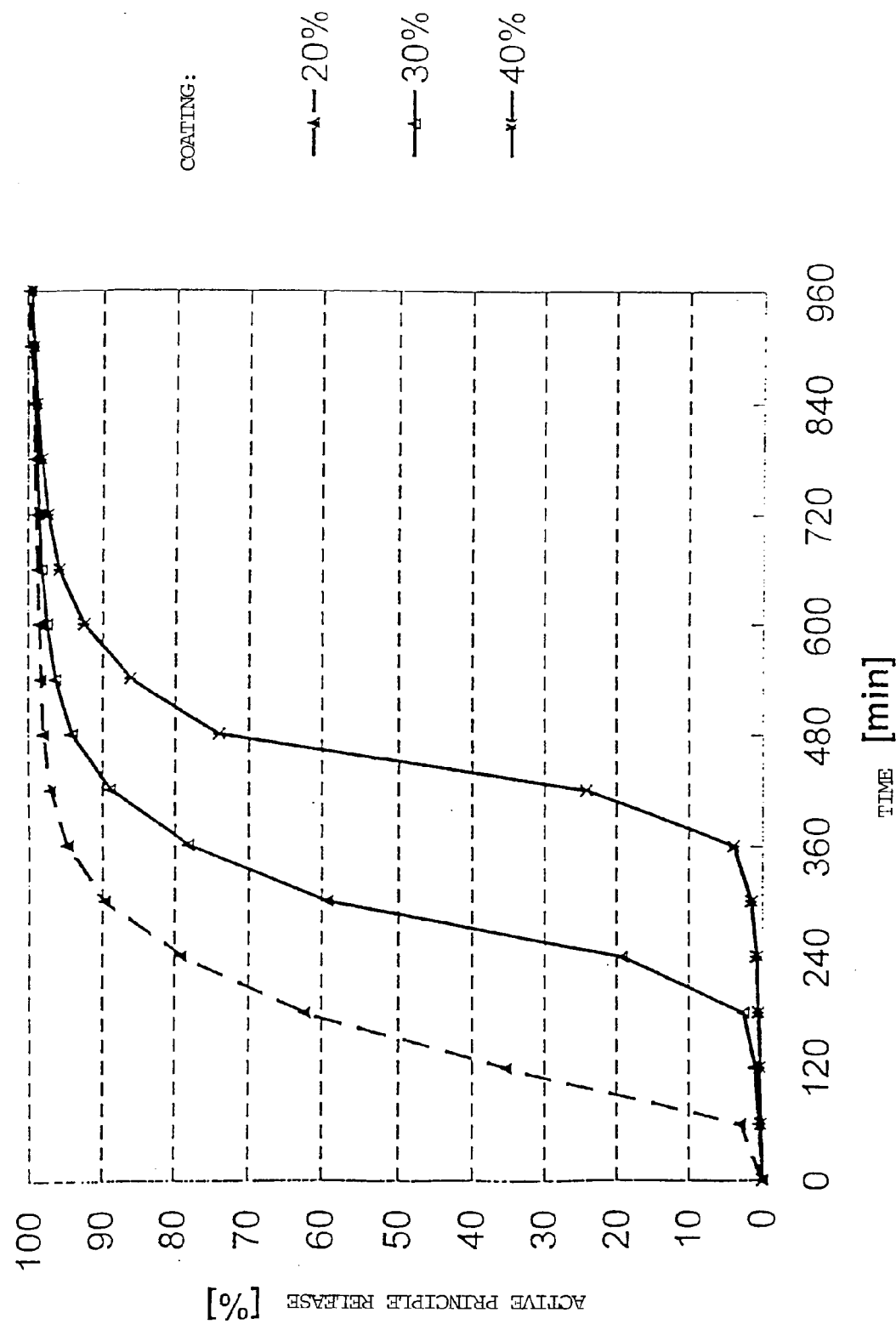
Figure 3:
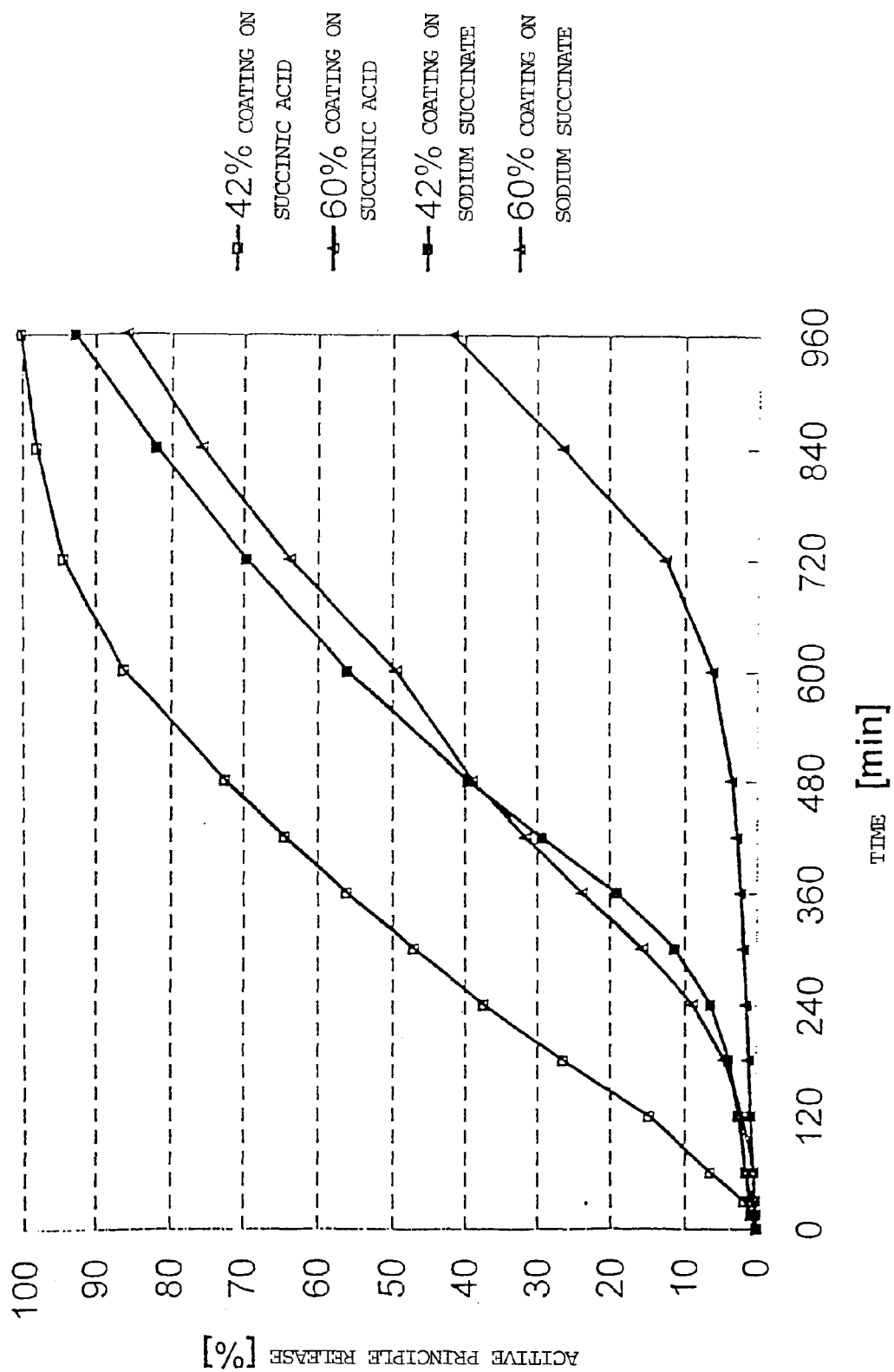
Figure 4:
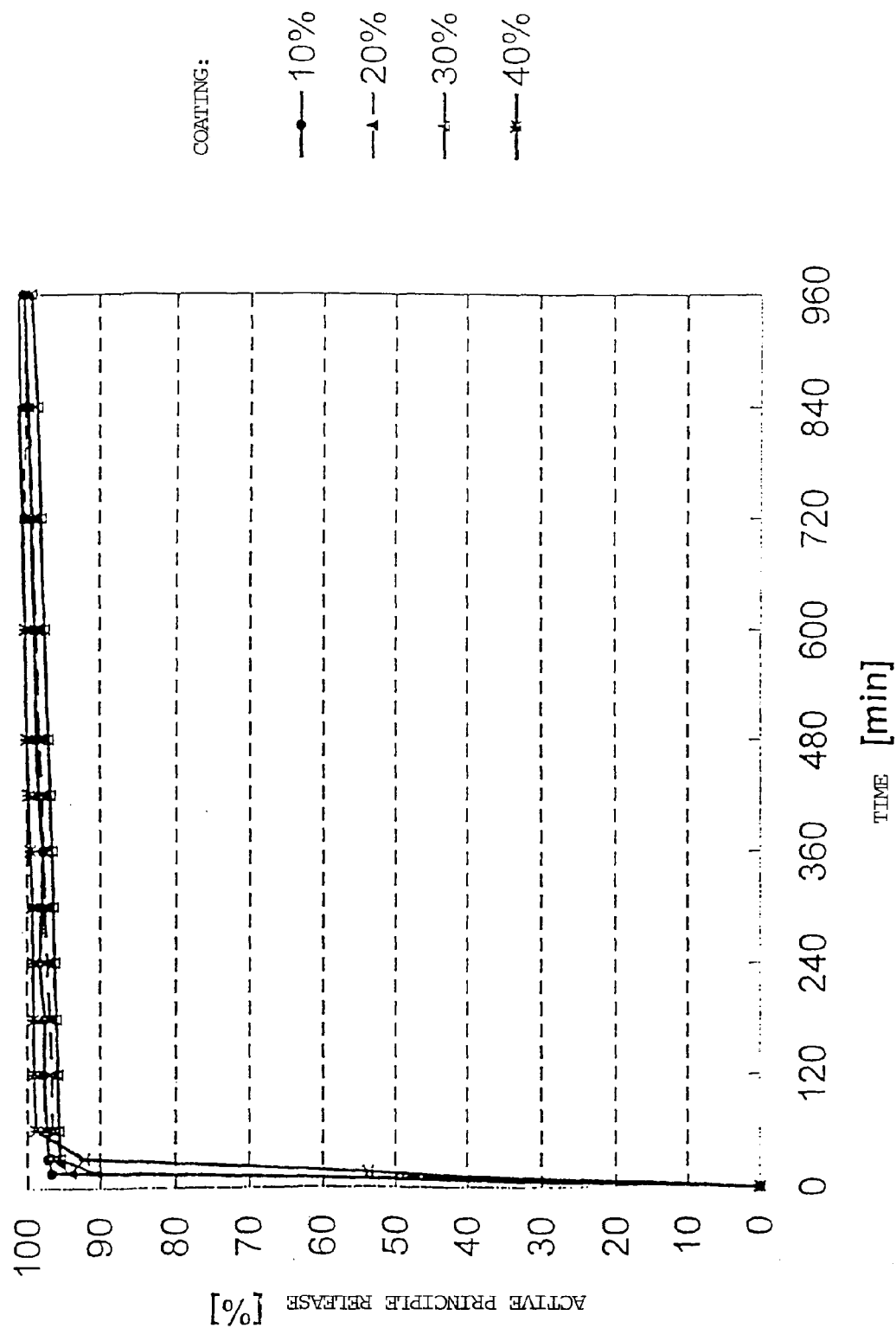
Figure 5:
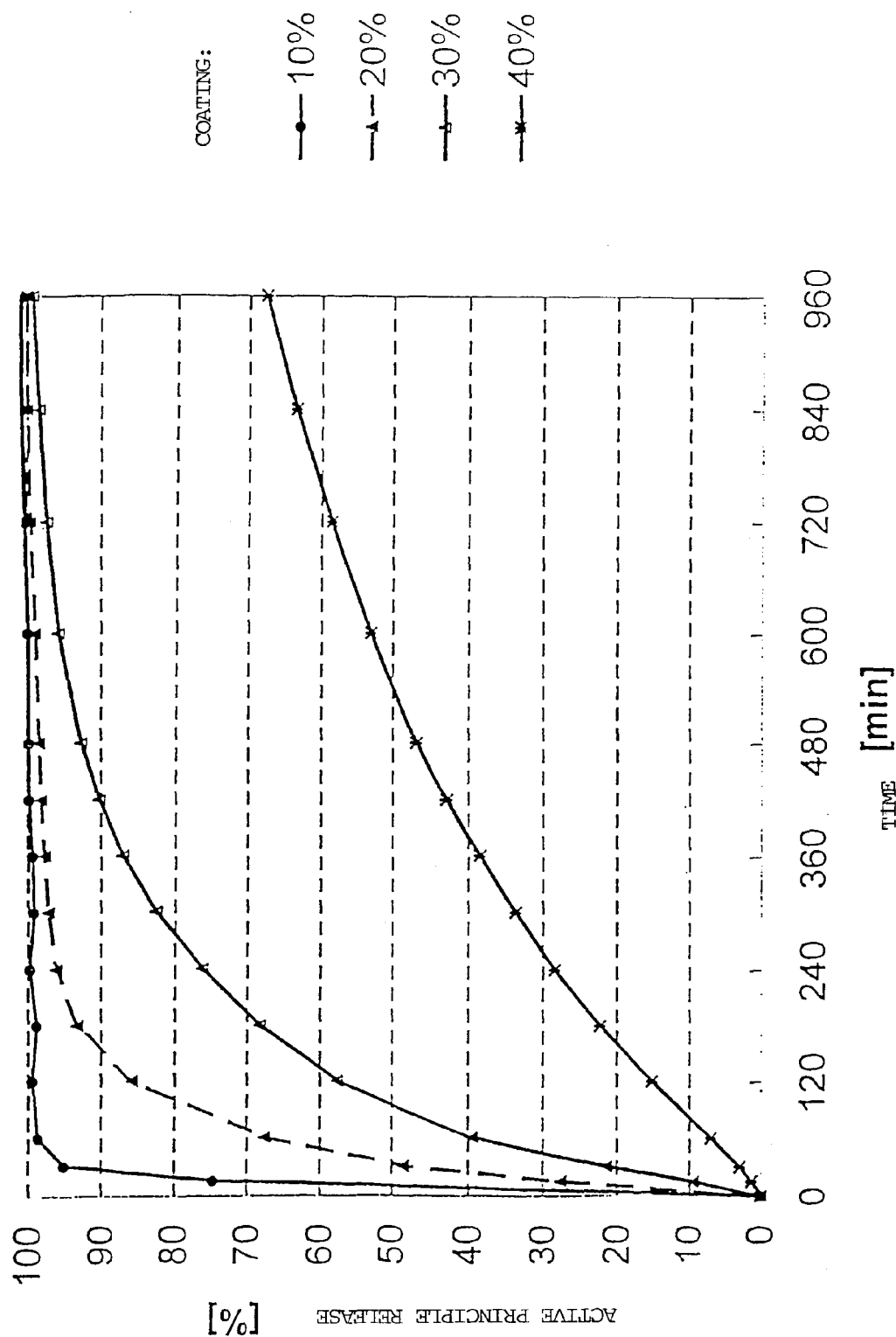

It was regarded as an object to improve the pharmaceutical preparations known from European Patent Applications 0463877 and 0436370. Among the objectives in this regard it was hoped to obtain, even with relatively small layer thicknesses, sigmoidal release curves that otherwise can only be achieved with larger applications of coating material. The object was achieved by a pharmaceutical formulation comprising (a) a core containing an active principle, if necessary a substrate and common pharmaceutical additives, and the salt of an organic acid, whose proportion of the core weight corresponds to 2.5 to 97.5 wt %, and (b) an outer coating film, which comprises one or more (meth)acrylate copolymers and, if necessary, common pharmaceutical adjuvants, wherein 40 to 100 wt % of the (meth)acrylate copolymers comprise 93 to 98 wt % of radically polymerized C1 to C4 alkyl esters of acrylic or methacrylic acid and 7 to 2 wt % of (meth)acrylate monomers with a quaternary ammonium group in the alkyl radical and if necessary can be present in a mixture with 1 to 60 wt % of one or more further (meth)acrylate copolymers, which are different from the above-mentioned (meth)acrylate copolymers, and which are composed of 85 to 100 wt % of radically polymerized C1 to C4 alkyl esters of acrylic or methacrylic acid and if necessary up to 15 wt % of further (meth)acrylate monomers with basic groups or acid groups in the alkyl radical.

OPERATION OF THE INVENTION

Cores (a)

In the simplest case, the core can be composed merely of the active principle and the salt of the organic acid. Usually it additionally contains a substrate such as a nonpareil and pharmaceutical adjuvants such as highly disperse silica gel or polyvinylpyrrolidone (PVP).

Thus core (a) comprises
- up to 97.5 to 2.5, preferably 80 to 5 wt % of active principle
- 2.5 to 97.5, preferably 5 to 80, especially 10 to 50 wt % of one or more salts of organic acid
- 0 to 95, preferably 10 to 50 wt % of pharmaceutical adjuvants
- 0 to 95, preferably 10 to 50 wt % of a substrate The cores can be manufactured by techniques such as direct pressing, extrusion and followed by forming to rounded shape, moist or dry granulation or direct pelleting (for example on plates) or by binding of powders (powder layering) on spherules (nonpareils) free of active principle or on particles containing active principle.

The pharmaceutical adjuvants included in addition to the active principle can be, for example, binders such as cellulose and derivatives thereof, polyvinylpyrrolidone (PVP), gelatins, (meth)acrylates, starches and derivatives thereof or sugar.

The cores can be homogeneous or can have a layered structure, wherein the active principle is preferably contained in the outer layer.

Salts of organic acids

The salts of organic acids used must be toxicologically safe and usable in pharmaceuticals. Alkali salts (ammonium, lithium, sodium, potassium) are preferred. The preferred type depends on the special formulation; besides the inventive functionality, however, the pharmacological effects of the ions must also be considered. Preferred are salts of weak organic acids such as citric acid, fumaric acid, formic acid, acetic acid, maleic acid, tartaric acid, glutaric acid or lactic acid.

Particularly suitable are sodium succinate, sodium citrate and sodium acetate. The use of acetic acid in the form of sodium acetate offers the advantage that processing can be achieved with a solid rather than with a liquid.

The type of acid controls the steepness of the active principle release curve, especially in the case of sigmoidal release curves.

In the inventive formulations, the salts are present as the outer layer of the core, bound by binders. They are applied by spraying from solution or by application of powder with simultaneous supply of binder solution.

Variations are also possible in individual cases, however, in which the active principle is applied in a mixture with the salts or a masking layer is applied between the active principle layer and the salt layer. Finally, the salt of the organic acid can also be applied on the core, so that it forms the outer layer.

The proportion of the salts of the organic acid(s) in the core weight amounts to 2.5 wt % to 97.5 wt %, preferably 5 to 80 wt %, especially 10 to 50 wt %.

Outer Coating Film (b)

The outer coating film comprises one or more (meth)acrylate copolymers and if necessary common pharmaceutical adjuvants such as plasticizers, pigments, pore-forming agents, wetting agents, release agents, etc.

The principle of the invention is based on a suspected interaction between the salt of an organic acid and a (meth)acrylate copolymer comprising 93 to 98 wt % of C1 to C4 alkyl esters of acrylic or methacrylic acid and 7 to 2 wt % of (meth)acrylate monomers with a quaternary ammonium group in the alkyl radical. In order to ensure this interaction, the said (meth)acrylate copolymers must comprise at least 40 wt % of the structure of the coating, in order to achieve the desired interaction. Such (meth)acrylate monomers are commercially available and have long been used for delayed-release coatings. They are practically insoluble in water. They can be used alone or in mixtures with other (meth)acrylate copolymers. If sigmoidal active principle release characteristics are to be obtained, coating (b) must comprise at least 80, preferably 90 or 100 wt % of the said copolymer type.

Preferred C1 to C4 alkyl esters of acrylic or methacrylic acid are methyl acrylate, ethyl acrylate, butyl acrylate, butyl methacrylate and methyl methacrylate.

2-Trimethylammoniumethyl methacrylate chloride is especially preferred as the (meth)acrylate monomer containing quaternary ammonium groups.

An appropriate copolymer can be formed, for example, from 50 to 70 wt % of methyl methacrylate, 20 to 40 wt % of ethyl acrylate and 7 to 2 wt % of trimethylammoniumethyl methacrylate chloride.

A preferred copolymer contains 65 wt % of methyl methacrylate, 30 wt % of ethyl acrylate and 5 wt % of 2-trimethylammoniumethyl methacrylate chloride (EUDRAGIT® RS).

Mixtures of (Meth)acrylate Copolymers

The mixture of the above-mentioned copolymers with further (meth)acrylate copolymers makes it possible to establish individual active principle release profiles. As examples, it is also possible to obtain, instead of sigmoidal curves, profiles with immediate release, continuous release profiles or profiles of zeroth order or first order. Depending on the active principle requirement, profiles intermediate between the said types can also be achieved.

According to the invention, outer coating film (b) therefore can be a mixture of the (meth)acrylate copolymers which comprise 93 to 98 wt % of C1 to C4 alkyl esters of acrylic or methacrylic acid and 7 to 2 wt % of (meth)acrylate monomers with a quaternary ammonium group in the alkyl radical and which are present in a proportion of at least 40 wt % with 1 to 60 wt %, preferably 40 to 60 wt % of one or more, preferably one, further (meth)acrylate copolymer or copolymers, which is or are composed of 85 to 100 wt % of C1 C4 alkyl esters of acrylic or methacrylic acid and if necessary up to 15 wt % of further (meth)acrylate monomers with functional basic groups or acid groups in the alkyl radical. When the content of basic groups or acid groups in the alkyl radical exceeds 15 wt %, the interactions among the components are influenced in an undesired or hardly foreseeable manner.

A suitable (meth)acrylate copolymer for such a mixture can be composed, for example, of 85 to less than 93 wt % of C1 to C4 alkyl esters of acrylic or methacrylic acid and more than 7 to 15 wt % of (meth)acrylate monomers with a quaternary ammonium group in the alkyl radical. Such (meth)acrylate monomers are commercially available and have long been used for delayed-release coatings.

A copolymer which specifically is suitable contains, for example, 60 wt % of methyl methacrylate, 30 wt % of ethyl acrylate and 10 wt % of 2-trimethylammoniumethyl methacrylate chloride (EUDRAGIT®) RL).

Another suitable (meth)acrylate copolymer for a mixture comprises 95 to 100 wt % of C1 to C4 alkyl esters of acrylic or methacrylic acid and 0 to 5 wt % of acrylic or methacrylic acid. Such (meth)acrylate monomers are commercially available.

Synthesis of (Meth)acrylate Copolymers in General

The (meth)acrylate copolymers are obtained in ways known in themselves by radical bulk, solution, bead or emulsion polymerization. They can exist in the form of extruded granules, ground powder, solution or dispersion.

Coatings

The polymer application depends on the size and surface area of the cores, on the solubility of the active principles and on the desired release profile. It ranges between 5 and 80 wt % relative to the core, preferably between 10 and 60%.

The coatings can be applied in multiple layers or as a mixture. Mixtures of the polymers make it possible to establish well-defined slopes in the second phase of the release profile. The content of quaternary ammonium groups in the coating controls the permeability and thus the diffusion rate of dissolved substances (McGinity, Ed., Aqueous Polymeric Coatings for Pharmaceutical Dosage Forms, Marcel Dekker, Inc., Chapter 4, pp. 208–216). The release rate becomes faster as the proportion of hydrophilic, quaternary ammonium groups is increased. In this way there is achieved an additional capability for control of active principle dosage in the second phase of the release profile.

Further Additives

These are used mainly as processing aids and are intended to ensure a reliable and reproducible manufacturing process as well as long shelf life. They can influence the permeability of the coatings, a property that can be used if necessary as an additional control parameter.

Plasticizers

Substances that are suitable as plasticizers usually have a molecular weight of between 100 and 20,000 and contain, in the molecule, one or more hydrophilic groups such as hydroxyl, ester or amino groups. Examples of suitable plasticizers are citric acid alkyl esters, glycerol esters, phthalic acid esters, sebacic acid esters, sucrose esters, sorbitan esters, dibutyl sebacate and polyethylene glycols 4000 to 20,000. Preferred plasticizers are triethyl citrate and acetyltriethyl citrate.

Are usually esters and liquid at room temperature:
citrates, phthalates, sebacates, castor oil Antiadhesive Agents These substances, which usually have lipophilic properties, are added to the spray suspensions and prevent agglomeration of the cores during film formation. Preferred are talc, ground silica gel or nonionic emulsifiers with an HLB value of between 3 and 8. The proportions range between 3 and 100 wt % relative to the polymer.

As examples of further additives there can be added, in ways known in themselves, stabilizers, dyes, antioxidants, wetting agents, pore-forming agents, pigments, brighteners, etc.

Application of the Film Coating

Application process takes place by spray application from organic solution, or aqueous dispersions by melting or by direct powder application. In this connection it is critical for execution that uniform, pore-free coatings be formed.

Application processes according to the prior art can be found in, for example, Bauer, Lehmann, Osterwald, Rothgan, "Coated Pharmaceutical Forms", Wissenschaftliche Verlagsgesellschaft mbH, Stuttgart, Chapter 7, pp. 165–196.

Properties, required tests and specifications relevant for application are listed in pharmacopeias.

Details can be found in common textbooks, such as:

Voigt, R. (1984): Textbook of Pharmaceutical Technology; Verlag Chemie Weinheim—Beerfield Beach/Fla.— Basel.

Sucker, H., Fuchs, P., Speiser, P.: Pharmaceutical Technology; Georg Thieme Verlag, Stuttgart (1991), especially Chapters 15 and 16, pp. 626–642.

Gennaro, A. R. (Editor), Remington's Pharmaceutical Sciences, Mack Publishing Co., Easton, Pa. (1985), Chapter 88, pp. 1567–1573.

List, P. H. (1982): Science of Pharmaceutical Forms, Wissenschaftliche Verlagsgesellschaft mbH Stuttgart.

Active Principles (Biologically Active Substances)

The pharmaceuticals used within the meaning of the invention are intended for administration in the human or animal body in order 1. to cure, alleviate, prevent or detect diseases, injuries, body damage or pathological conditions, 2. to allow the nature, condition or functions of the body or mental conditions to be discerned,
3. to replace active principles or body fluids generated by the human or animal body,
4. to combat, eliminate or render harmless pathogens, parasites or substances foreign to the body or
5. to influence the nature, condition or functions of the body or mental conditions.

Common pharmaceuticals can be found in reference works such as the Red List or the Merck Index.

According to the invention there can be used all active principles that satisfy the desired therapeutic effect within the meaning of the definition given hereinabove and that have adequate thermal stability.

Without claiming completeness, important examples (groups and individual substances) are the following:
analgesics, antiallergics, antiarrhythmics antibiotics, chemotherapeutics, antidiabetics, antidotes, antiepileptics, antihypertensives, antihypotensives, anticoagulants, antimycotics, antiphlogistics, beta receptor blockers, calcium antagonists and ACE inhibitors, broncholytics/antiasthmatics, cholinergics, corticosteroids (internal), dermatics, diuretics, enzyme inhibitors, enzyme preparations and transport proteins, expectorants, geriatrics, gout remedies, flu medicines, hormones and their inhibitors, hypnotics/sedatives, cardiacs, lipid-lowering drugs, parathyroid hormones/calcium metabolism regulators, psychopharmaceuticals, sex hormones and their inhibitors, spasmolytics, sympatholytics, sympathomimetics, vitamins, wound medications, cytostatics.

Preferred active principles for slow release of active principles are:
nifedipine, diltiazem, theophylline, diclofenac sodium, ketoprofen, ibuprofen, indomethacin, diltianzem, ambroxol, terbutaline, vincamine, propranolol, pentoxifylline, codeine, morphine, etilefrin, carbamazepine or the therapeutically used salts thereof.

Application Forms and Further Embodiments

In principle the described pharmaceutical forms can be administered directly by oral application. In the case of multiparticulate forms (multi unit dosage forms), however, further processing steps are performed subsequently.

The coated forms prepared according to the invention can be filled as individual doses into gelatin capsules and bags (sachets) or into appropriate multi-dose containers with dispensing device. Ingestion takes place in solid form or as a suspension in liquids.

By pressing there are obtained from granulates, if necessary after mixing in further adjuvants, tablets that disintegrate after ingestion and release the retarded subunits. Also conceivable is the embedding of agglomerates in polyethylene glycol or lipids for preparation of suppositories or vaginal pharmaceutical forms.

In addition, coatings (b) can also be combined with or coated by prior art coatings. Suitable for this purpose are in particular (meth)acrylate copolymers which contain 10 to 60 wt % of methacrylic acid groups and otherwise are composed of, for example, methyl methacrylate and/or ethyl acrylate (EUDRAGIT® type L or S). In this way taste-masking properties or formulations for selective releases in the colon can be additionally achieved in combination with the inventive formulations.

EXAMPLES

Copolymers Used
Copolymer 1:
65 wt % of methyl methacrylate, 30 wt % of ethyl acrylate and 5 wt % of trimethylammoniumethyl methacrylate chloride (EUDRAGIT® RS).

Copolymer 2:
60 wt % of methyl methacrylate, 30 wt % of ethyl acrylate and 10 wt % of trimethylammoniumethyl methacrylate chloride (EUDRAGIT® RL).

Copolymer 3:
30 wt % of ethyl acrylate, 69 wt % of methyl methacrylate and 1 wt % of methacrylic acid (EUDRAGIT® NE 30D).

Preparation of Coated Theophylline Preparations

The preparation of the active-principle-containing pellet cores is achieved in a manner known in itself in a conventional sugar-coating pan by the sprinkling process. In this process the substrate cores (nonpareils) are rotated in the pan and built up to pellets with the powder mixture (sprinkling) while continuous humidification is performed with the binder solution (spraying, nozzle diameter 1 mm, spraying pressure 0.5 bar, spraying speed 3 to 6 g/min). Thereafter the product is dried in the drying cabinet (24 hours at 40° C.) and the needed particle-size fraction is collected by sieving.

Nonpareils (0.5 to 0.6 mm) were used as substrates in all examples. Thereon there was applied theophylline as the active principle as well as various proportions of the respective organic acid salt being used. As pharmaceutical adjuvants there were used a polyvinylpyrrolidone (Kollidon 25) in, and highly disperse silica gel (Aerosil 200) or sucrose. The sprinkling time ranged between 77 and 142 minutes at pan speeds of 40 rpm.

The coating is applied by known techniques in a fluidized-bed apparatus. Aqueous dispersions with a copolymer content of 30 wt % were used. In addition, triethyl citrate was used as plasticizer and talc as release agent.

Measurement of the Theophylline Release

Determination of the active principle release was performed in a manner known in itself from the European Pharmacopeia in a paddle apparatus at a speed of 100 rpm in purified water or phosphate buffer of pH 6.8. The quantity of active principle released was determined photometrically. The measurement period was adapted to the adjusted release profile and ranged between 10 and 24 hours, with measurements every 1 or 2 hours as the case may be. After completion of the determination, the test liquid containing the remaining pellet residues was homogenized and the quantity of active principle present therein was used as 100% reference value for the calculation.

Example 1

Release curve of the influence of various proportions (21, 32 and 43 wt %) of sodium acetate in theophylline/sodium acetate cores with a coating application of 30 wt % of copolymer 1.

Example 2

Release curve of the influence of various layer thicknesses (20, 30 and 40 wt %) of copolymer 1 on theophylline/sodium acetate cores.

Example 3

Comparison of the release of theophylline from theophylline/sodium succinate (Na succinate) and theophylline/succinic acid preparations with 42 and 0.60 wt % coating applications of copolymer 1.

Example 4

Release curve of the influence of various layer thicknesses (10, 20, 30 and 40 wt %) of a mixture (1:1) of copolymer 1 and copolymer 2 on theophylline/sodium acetate cores.

Example 5

Release curve of the influence of various layer thicknesses (10, 20, 30 and 40 wt %) of a mixture (1:1) of copolymer 1 and copolymer 3 on theophylline/sodium acetate cores.

The recipes for Examples 1 to 5 are summarized in the following table (all values in g):

| Example | 1 | 2 | 3 | 4 | 5 |
|---|---|---|---|---|---|
| CORES | | | | | |
| 1) Sprinkling mixture | | | | | |
| Nonpareils | 700 | 700 | 700 | 700 | 700 |
| Theophylline | 901/675/450 | 675 | 420 | 675 | 675 |
| Na acetate | 450/675/901 | 675 | — | 675 | 675 |
| Na-succinate/succinic acid | | | 960/700 | | |
| Kollidon 25 | 42 | 42 | 43/35 | 42 | 42 |
| Aerosil 200 | 7 | 7 | 7/6 | 7 | 7 |
| 2) Binder solution | | | | | |
| Kollidon 30 | 20 | 20 | — | 20 | 20 |
| Sucrose | — | — | 276/97 | — | — |
| Ethanol | — | — | 135/28 | — | — |
| Water | 380 | 380 | 430/85 | 380 | 380 |
| CORES + COATINGS | | | | | |
| Quantity of coated cores | 500 | 500 | 500 | 500 | 500 |
| Copolymer 1 dispersion, 30% | 500 | 333/500/667 | 1005 | 83/167/250/333 | 83/167/250/333 |
| Copolymer 2 dispersion, 30% | — | — | — | 125/167/250/333 | — |
| Copolymer 3 dispersion, 30% | — | — | — | — | 83/167/250/333 |
| Triethyl citrate | 30 | 27/40/53 | 38 | 10/20/30/40 | 10/20/30/40 |
| Talc | 75 | 50/75/100 | 159 | 25/50/75/100 | 25/50/75/100 |
| Water | 670 | 447/670/893 | 1179 | 225/447/670/893 | 225/447/670/893 |

What is claimed is:

1. A pharmaceutical formulation comprising
   (a) a core containing an active principle and 2.5 to 97.5 wt % of at least one salt of an organic acid, based on the core weight, and
   (b) an outer coating film, which comprises
   40 to 100 wt % of at least one (meth)acrylate copolymer (1) which comprises 93 to 98 wt % of radically polymerized C1 to C4 alkyl esters of acrylic or methacrylic acid and 7 to 2 wt % of (meth)acrylate monomers with a quaternary ammonium group in the alkyl radical, and optionally
   1 to 60 wt % of at least one (meth)acrylate copolymer (2), different from (meth)acrylate copolymer (1), and which comprises 85 to 100 wt % of radically polymerized C1 to C4 alkyl esters of acrylic or methacrylic acid and up to 15 wt % of (meth)acrylate monomers with basic groups or acid groups in the alkyl radical.

2. A formulation according to claim 1, wherein the (meth)acrylate copolymer component of the outer coating film (b) is a mixture of
   99 to 40 wt % of said (meth)acrylate copolymer (1), and
   1 to 60 wt % of said (meth)acrylate copolymer (2), which comprises 85 to less than 92 wt % of C1 to C4 alkyl esters of acrylic or methacrylic acid and more than 7 to 15 wt % of (meth)acrylate monomers with a quaternary ammonium group in the alkyl radical.

3. A formulation according to claim 1, wherein the (meth)acrylate copolymer component of the outer coating film (b) is a mixture of
   99 to 40 wt % of said (meth)acrylate copolymer (1), and
   1 to 60 wt % of said (meth)acrylate copolymer (2), which comprises 95 to 100 wt % of C1 to C4 alkyl esters of acrylic or methacrylic acid and 0 to 5 wt % of acrylic or methacrylic acid.

4. A formulation according to claim 1, wherein the (meth)acrylate monomer with a quaternary ammonium group in the alkyl radical comprises trimethylammoniumethyl methacrylate chloride.

5. A formulation according to claim 1, wherein the salt of the organic acid is at least one of an ammonium, lithium, sodium or potassium salt, of citric acid, fumaric acid, formic acid, acetic acid, maleic acid, succinic acid, tartaric acid, glutaric acid or lactic acid.

6. A formulation according to claim 1, which is pressed into a tablet.

7. A formulation according to claim 1, which is encapsulated by a gelatin capsule.

8. A formulation according to claim 1, which is additionally encapsulated with a (meth)acrylate copolymer which contains 10 to 60 wt % of methacrylic acid radicals.

9. A formulation according to claim 1, wherein the salt of the organic acid forms the outer layer of the core.

10. A formulation according to claim 1, wherein the core comprises:
    97.5 to 2.5 wt % of the active principle, and additionally comprises 0 to 95 wt % of pharmaceutical adjuvants, and 0 to 95 wt % of a substrate.

11. A formulation according to claim 10, wherein the core comprises:
    80 to 5 wt % of the active principle, 5 to 80 wt % of the at least one salt of an organic acid, 10 to 50 wt % of the pharmaceutical adjuvants, and 10 to 50 wt % of the substrate.

12. A formulation according to claim 11, wherein the core comprises 10 to 50 wt % of the at least one salt of an organic acid.

13. A formulation according to claim 1, wherein the core is homogeneous or has a layered structure.

14. A formulation according to claim 13, wherein the core has a layered structure and the active principle is contained in the outer layer of the core.

15. A formulation according to claim 1, wherein the salt of an organic acid is at least one of sodium succinate, sodium citrate and sodium acetate.

16. A formulation according to claim 15, wherein the salt of an organic acid comprises sodium succinate.

17. A formulation according to claim 1, wherein the salt of an organic acid comprises sodium citrate.

18. A formulation according to claim 1, wherein the salt of an organic acid comprises sodium acetate.

19. A formulation according to claim 1, wherein the active principle comprises theophylline.

* * * * *